United States Patent
Ko (10) Patent No.: US 9,943,368 B2
(45) Date of Patent: Apr. 17, 2018

(54) INTENSE PULSED LIGHT APPARATUS CAPABLE OF CONTROLLING ENEGY LEVEL WITH SCR

(75) Inventor: YoungSan Ko, Seongnam-si (KR)

(73) Assignee: Yongsan Ko, Seongnam-si, Gyeonggi-Do (KR)

( * ) Notice: Subject to any disclaimer, the term of this patent is extended or adjusted under 35 U.S.C. 154(b) by 1169 days.

(21) Appl. No.: 13/696,934

(22) PCT Filed: May 25, 2011

(86) PCT No.: PCT/KR2011/003812
§ 371 (c)(1),
(2), (4) Date: Nov. 8, 2012

(87) PCT Pub. No.: WO2011/152628
PCT Pub. Date: Dec. 8, 2011

(65) Prior Publication Data
US 2013/0066307 A1    Mar. 14, 2013

(30) Foreign Application Priority Data

Jun. 4, 2010 (KR) .................. 10-2010-0052946

(51) Int. Cl.
*A61B 18/18* (2006.01)
*A61B 18/20* (2006.01)
(Continued)

(52) U.S. Cl.
CPC .......... *A61B 18/203* (2013.01); *A61N 5/0613* (2013.01); *H05B 41/30* (2013.01);
(Continued)

(58) Field of Classification Search
CPC .......... A61B 18/203; A61B 2018/0047; A61N 2005/0654; A61N 5/0613; A61N 5/0616; H05B 41/30
(Continued)

(56) References Cited

U.S. PATENT DOCUMENTS 3,771,017 A    11/1973    Switsen
3,781,632 A    12/1973    Charboneau
(Continued)

FOREIGN PATENT DOCUMENTS

EP    0043112       1/1982
EP    0043112 A2    1/1982
(Continued)

OTHER PUBLICATIONS

European Search Report for Application No. EP 11 78 9986 dated Nov. 11, 2013.
(Continued)

*Primary Examiner* — Michael Carey
*Assistant Examiner* — Pamela M Bays
(74) *Attorney, Agent, or Firm* — Cantor Colburn LLP (57) ABSTRACT

The present invention relates to an IPL apparatus that is used as a hair removing machine or cures skin ailments by periodically irradiating Xenon lamp light on the user's skin, the IPL apparatus comprises: a double-voltage unit which has a double-voltage capacitor, and outputs a high voltage by superposing an inputted supply voltage with a voltage charged in the double-voltage capacitor; a charging capacitor which charges energy for turning on a Xenon lamp by accumulating electric charges supplied from the double-voltage unit; a reference voltage generator which sets a charging voltage level charged in the charging capacitor; and a switch unit which is positioned between the double-voltage unit and the charging capacitor, and switches on and off the movement of the electric charges to the charging capacitor from the double-voltage unit by setting an output of the reference voltage generator to a control signal.

9 Claims, 6 Drawing Sheets (51) Int. Cl.
*A61N 5/06* (2006.01)
*H05B 41/30* (2006.01)
*A61B 18/00* (2006.01)

(52) U.S. Cl.
CPC ............ *A61B 2018/0047* (2013.01); *A61B 2018/00476* (2013.01); *A61N 5/0616* (2013.01); *A61N 2005/0654* (2013.01)

(58) Field of Classification Search
USPC .............................................. 606/9
See application file for complete search history.

(56) References Cited

U.S. PATENT DOCUMENTS

| | | | |
|---|---|---|---|
| 3,870,924 A * | 3/1975 | Helmuth | H05B 41/32 315/200 A |
| 3,885,573 A * | 5/1975 | Hara | A61N 1/40 607/68 |
| 4,199,710 A | 4/1980 | Knoll | |
| 4,286,263 A * | 8/1981 | Lindberg | G09F 9/30 345/2.2 |
| 4,618,803 A | 10/1986 | Hardy | |
| 5,118,995 A | 6/1992 | Hauser | |
| 5,391,191 A * | 2/1995 | Holmstrom | A61N 1/37 607/28 |
| 6,104,147 A | 8/2000 | Nakamura et al. | |
| 6,608,452 B1 | 8/2003 | Holmes | |
| 2002/0105283 A1* | 8/2002 | Murakami | H05B 41/2985 315/224 |
| 2004/0167498 A1 | 8/2004 | Azar et al. | |
| 2005/0245997 A1 | 11/2005 | Holjo et al. | |
| 2006/0074468 A1* | 4/2006 | Neev | A61B 18/203 607/90 |
| 2010/0013404 A1 | 1/2010 | Redjebian | |
| 2010/0060187 A1 | 3/2010 | Newman, Jr. et al. | |

FOREIGN PATENT DOCUMENTS

| | | |
|---|---|---|
| JP | 05283774 A | 10/1993 |
| JP | 07281769 A | 10/1995 |
| JP | 09220292 A | 8/1997 |
| JP | 2005524499 A | 8/2005 |
| KR | 101998058057 A | 9/1998 |
| KR | 2020000011066 B | 6/2000 |
| KR | 200309522 A | 3/2003 |
| KR | 20-0392330 | 8/2005 |
| KR | 200392330 Y1 | 8/2005 |
| KR | 100525292 B1 | 10/2005 |
| KR | 100638735 B1 | 10/2006 |
| KR | 1020090028287 A | 3/2009 |
| KR | 10-2009-0037543 | 4/2009 |
| KR | 1020090037543 A | 4/2009 |
| KR | 1020090106714 A | 10/2009 |
| KR | 10-2010-0127927 | 12/2010 |

OTHER PUBLICATIONS

"Voltage doubler rectifier circuit", NAVER encyclopedia of Knowledge, file:///C:/Users/KYEONG~1/AppData/Local/Temp/Low/VXCH6WM8.htm, Sep. 18, 2014.
Written Opinion-PCT/KR2011/003812 dated Feb. 6, 2012.
International Search Report-PCT/KR2011/003812 dated Feb. 6, 2012.
European Office Action for Application No. 11 789 986.4-1666 dated Aug. 11, 2017, citing the above reference(s).

* cited by examiner

INTENSE PULSED LIGHT APPARATUS CAPABLE OF CONTROLLING ENEGY LEVEL WITH SCR

TECHNICAL FIELD

The present invention relates to an intense pulsed light apparatus capable of controlling an energy level with an SCR, and more specifically, to an intense pulse light apparatus having a Xenon flash driving circuit capable of controlling a voltage controlling-type energy level with an SCR without employing a noise filter and a high-power output voltage-controlled constant voltage power supply circuit.

BACKGROUND ART

In the initial stage, many laser apparatuses were introduced to treat skin ailments. These laser apparatuses are appropriate for curing a particular skin ailment by selecting the laser light of a wavelength necessary for treating specific ailments and locally irradiating the selected laser light on the corresponding skin part to be treated. However, said laser apparatuses have a lot of side effects, and particularly, it is hard to irradiate laser beams on the skin that has various skin ailments. That is to say, because each ailment needs proper laser beams, these ailments should be treated by using several laser beams if the patient wants to be treated due to the freckles or blemishes, the expanded blood vessels, and fine wrinkles or large pores on his or her face.

To solve such drawbacks, an intense pulsed light (hereinafter, IPL) apparatus, which simply cures various skin ailments by irradiating diverse wavelengths of lights at a time, has been developed by an American doctor Bitter, and is being widely used at the moment. The IPL apparatus employs a lamp flash that emits light having a wavelength of 350 nm to 1200 nm, and adjusts the wavelength of the emitted light with a filter, and generally, as the irradiation lamp, a Xenon lamp irradiates laser beams on the skin for three seconds, two to three times approximately.

Like mentioned above, when the IPL apparatus irradiates laser beams with the Xenon lamp, the amount of energy that is irradiated at a time should be controlled at a desired level. Further, the IPL apparatus has to supply regular power to a Xenon flash circuit in order to emit the irradiation energy of which the level is determined. For the lamp flash driving circuit of the IPL apparatus, a PAM (Pulse Amplitude Modulation) driving circuit mode, a PWM (Pulse Width Modulation) driving circuit mode, and a mixed type thereof are used.

Figure 1:
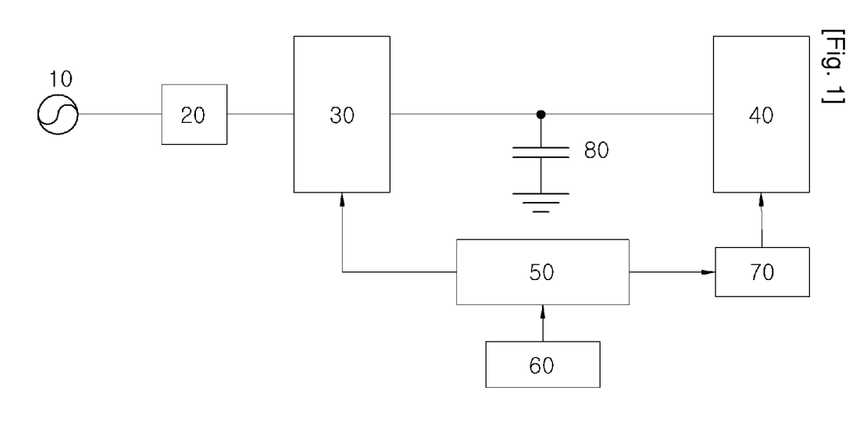
FIG. 1 is a driving circuit diagram of a prior IPL apparatus that employs a PAM driving mode.

FIG. 1 is a driving circuit diagram of a prior IPL apparatus that employs a PAM driving mode. Power supplied from a supply voltage 10 ranging from 100V to 240V is inputted to an output voltage-controlled constant voltage supplier 30 (for example, SMPS (Switching Mode Power Supply)) after noise has been removed by a noise filter 20. The output voltage-controlled constant voltage supplier 30 converts the inputted power into stable DC power, and supplies the DC power to a capacitor 80. When the user adjusts the irradiation energy of a Xenon lamp through a user interface 60, a corresponding adjustment signal is inputted to a controller 50, and the controller 50 precisely adjusts an output voltage of the output voltage-controlled constant voltage supplier 30 according to the adjustment signal. Further, if the controller 50 drives a Xenon lamp flash unit 40 through a trigger 70 at every proper time by using the energy supplied to the capacitor 80 from the output voltage-controlled constant voltage supplier 30, the energy stored in the capacitor 80 is instantly supplied to the Xenon lamp flash unit 40. Hence, if a voltage applied to the capacitor 80 is adjusted, a desired level of the energy supplied to the Xenon lamp flash unit 40 is obtained. In the PAM driving mode of FIG. 1, the amount of energy (that is, voltage values on both ends of the capacitor 80) supplied to the Xenon lamp flash unit 40 is adjusted in such a manner that the amount of energy delivered to the user's skin can be controlled precisely.

Figure 2:
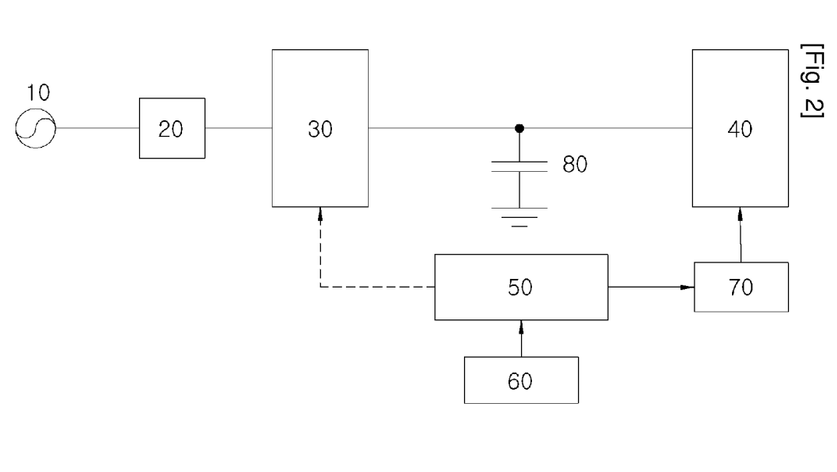
FIG. 2 is a driving circuit diagram of a prior IPL apparatus that employs a PWM driving mode.
Figure 3:
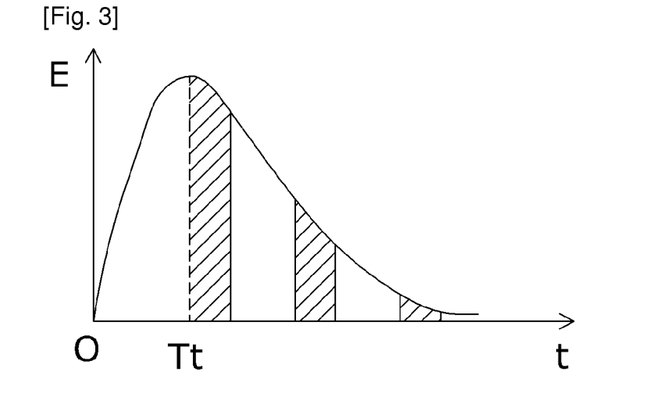
FIG. 3 is a graph for illustrating the amount of energy charged and discharged in accordance with time in a Xenon lamp flash unit of the prior IPL apparatus that employs the PWM driving mode shown in FIG. 2.

FIG. 2 is a driving circuit diagram of a prior IPL apparatus that employs a PWM driving mode. Power supplied from a supply voltage 10 ranging from 100V to 240V is inputted to an output voltage-controlled constant voltage supplier 30 (for example, SMPS (Switching Mode Power Supply)) after noise has been removed by a noise filter 20. The output voltage-controlled constant voltage supplier 30 converts the inputted power into stable DC power, and supplies the DC power to a capacitor 80. When the user adjusts the irradiation energy of a Xenon lamp through a user interface 60, a corresponding adjustment signal is inputted to a controller 50, and the controller 50 outputs a trigger signal for performing a proper PWM driving process to a trigger 70, and precisely controls the amount of energy supplied to the Xenon lamp flash unit 40. In this case, the controller 50 may adjust a charging voltage by transmitting a control signal even to the output voltage-controlled constant voltage supplier 30 when necessary. FIG. 3 is a graph for illustrating the amount of energy charged and discharged in accordance with time in the Xenon lamp flash unit 40 of the prior IPL apparatus that employs the PWM driving mode shown in FIG. 2. Like illustrated in FIG. 3, it could be understood that the Xenon lamp flash unit 40 is driven only in the oblique sections from the moment when a trigger signal is applied, while the energy is charged to the trigger time Tt from time 0. That is to say, in the PWM driving mode of FIG. 2, by controlling the width and intervals of the oblique time for the amount of energy supplied to the Xenon lamp flash unit 40, it is possible to precisely adjust the amount of energy delivered to the user's skin.

However, the prior IPL apparatus that employs the PAM driving mode in FIG. 1, the prior IPL apparatus that employs the PWM driving mode in FIG. 2, and the prior IPL apparatus that employs the mixed type thereof use the output voltage-controlled constant voltage supplier 30 in order to supply stable power to the capacitor 80. In this case, because the IPL is characterized in that DC current values outputted from the output voltage-controlled constant voltage supplier 30 use hundreds of milliamperes (mA) to tens of amperes (A), a high-capacity power source should be switched, whereby a high-priced output voltage-controlled constant voltage supplier 30 is essential. Further, it is problematic because an expensive noise filter 20 has to be equipped in order to remove noise of the power that is supplied to the high-capacity output voltage-controlled constant voltage supplier 30. Such a problem is now emerging since the more expensive noise filter 20 and the higher-priced output voltage-controlled constant voltage supplier 30 should be used if the capacitor 80 has to be charged at a faster speed in order to more often turn on the Xenon lamp flash unit 40 at every second.

In addition, when the output of the IPL apparatus is increased, the IPL apparatus may be used as a hair removing machine for removing hairs on legs, arms and the like. However, if the IPL apparatus is used as the hair removing machine, a higher output is necessary. Thus, when the driving circuit of the prior IPL apparatus is used, the higher-priced output voltage-controlled constant voltage supplier (30) and the more expensive noise filter (20) should be provided as well.

DISCLOSURE OF THE INVENTION

Technical Problem

To solve such problems, it is therefore an object of the present invention to provide an IPL apparatus capable of controlling an energy level with an SCR, which can stably provide power to a Xenon lamp flash unit even by supplying power to a capacitor without an output voltage-controlled constant voltage supplier.

In addition, it is another object of the present invention to provide an IPL apparatus capable of controlling an energy level with an SCR, which can be equipped with a driving circuit for stably increasing an output voltage of the IPL apparatus within a relatively short time even in an area having a power voltage ranging from 100V to 120V, which is deficient to obtain high energy, or if there is a change owing to an unstable voltage of the inputted power.

Solution to Problem

To achieve the above purpose of the present invention, in an IPL apparatus that is used as a hair removing machine or cures skin ailments by periodically irradiating Xenon lamp light on the user's skin, the IPL apparatus comprises: a double-voltage unit which has a double-voltage capacitor, and outputs a high voltage by superposing an inputted supply voltage with a voltage charged in the double-voltage capacitor; a charging capacitor which charges energy for turning on a Xenon lamp by accumulating electric charges supplied from the double-voltage unit; a reference voltage generator which sets a charging voltage level charged in the charging capacitor; and a switch unit which is positioned between the double-voltage unit and the charging capacitor, and switches on and off the movement of the electric charges to the charging capacitor from the double-voltage unit by setting an output of the reference voltage generator to a control signal.

Desirably, it is better to provide, in front of the reference voltage generator, a constant current supply unit for supplying a regular current to the reference voltage generator.

In order to supply more stable DC power to the controller, it is better to further comprise a constant voltage supplier for inputting power outputted from the noise filter and supplying the power to the controller, but the constant voltage supplier used in the present invention is to stably supply power to the controller. Thus, the constant voltage supplier having small capacities, that is, roughly tens of watts, may be accepted in such a manner the driving circuit of the Xenon lamp flash unit can be designed at a low price.

Driving circuit of the Xenon lamp flash unit according to the present invention can be driven PAM (Pulse Amplitude Modualation) mode by controlling reference voltage or PWM (Pulse Width Modulation) mode by adjusting the interval of trigger signal using controller.

Advantageous Effects

According to the present invention, the IPL apparatus enables a stable IPL apparatus driving function even through an inexpensive circuit configuration, which can accumulate electric charges in the capacitor without a high-power output voltage-controlled constant voltage power supplier and exactly sense a voltage applied to the capacitor, so that the corresponding voltage may reach a regular value, and can radiate the desired energy by controlling discharge time or supplying a desired voltage to the Xenon lamp flash unit. Further, according to the present invention, the IPL apparatus is easily implemented in PAM and PWM driving modes through the same circuit configuration.

Besides, according to the present invention, since the IPL apparatus employs a double-voltage unit, the IPL apparatus smoothly drives the Xenon lamp flash unit by receiving sufficient energy within a relatively short time irrespective of an area, where a voltage value of a supply voltage is unstable or a low supply voltage ranging from 100V to 120V is used.

DESCRIPTION OF REFERENCE NUMERALS AND SIGNS

10: SUPPLY VOLTAGE
20: NOISE FILTER UNIT
30: OUTPUT VOLTAGE-CONTROLLED CONSTANT VOLTAGE SUPPLIER
35: CONSTANT VOLTAGE SUPPLY UNIT
38: CONSTANT CURRENT SUPPLY UNIT
40: XENON LAMP FLASH UNIT
50: CONTROLLER
60: USER INTERFACE UNIT
70: TRIGGER UNIT
80: CHARGING CAPACITOR
90: REFERENCE VOLTAGE GENERATOR
91: RECTIFICATION UNIT
93: SMOOTHING UNIT
95: VOLTAGE DIVIDER
97: ANALOT TO DIGITAL CONVERTER
110: DOUBLE-VOLTAGE UNIT

115: INPUT WAVE TIMING UNIT
125: ZENER TEMPERATURE COMPENSATION CIRCUIT UNIT
195: VOLTAGE DIVIDER

DESCRIPTION OF EXEMPLARY EMBODIMENTS

Hereinafter, the advantages, the features, and the preferred embodiments of the present invention will be described in detail with reference to the accompanying drawings.

Figure 4:
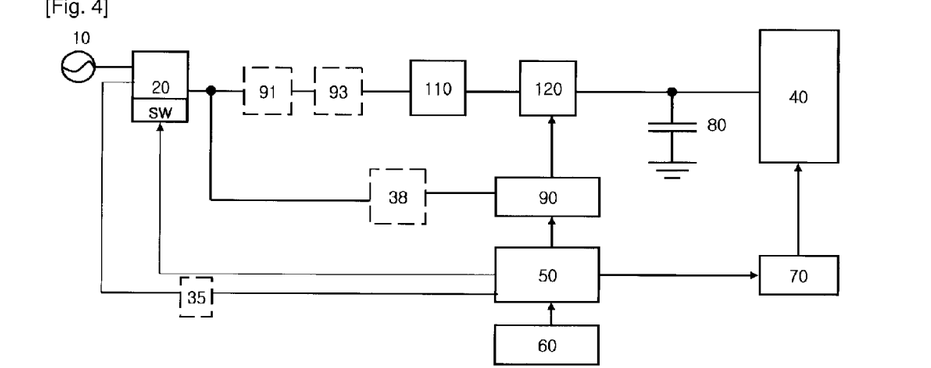
FIG. 4 is one embodiment of a driving circuit diagram of an IPL apparatus in accordance with the present invention.

FIG. 4 is one embodiment of a driving circuit diagram of an IPL apparatus in accordance with the present invention. According to the present invention, the IPL apparatus comprises a noise filter unit 20, a double-voltage unit 110, a switch unit 120, a charging capacitor 80, a reference voltage generator 90, a controller 50, a user interface unit 60, a trigger unit 70 and a Xenon lamp flash unit 40.

The double-voltage unit means a voltage doubler, and the charging capacitor means a storage capacitor.

Additionally, the present invention may further comprise a rectification unit 91, a smoothing unit 93, a constant voltage supply unit 35, and a constant current supply unit 38.

The noise filter unit 20 is a circuit element for removing noise from an inputted supply voltage 10 ranging from 100V to 240V, and an output of the noise filter unit 20 passes through the rectification unit 91 and the smoothing unit 93 and supplies to the double-voltage unit 110. The rectification unit 91 and the smoothing unit 93 are partially contributed to form double-voltage as will be described later on FIG. 10. It is needless to say that the output of the noise filter 20 is supplied to the double-voltage unit 110 in a circuit where the rectification unit 91 and the smoothing unit 93 are not equipped. The double-voltage unit 110 is a circuit for outputting the inputted supply voltage after increasing a peak value of the supply voltage double times or more. The switch unit 120 is turned on and off according to an output signal of the reference voltage generator 90, and charges the charging capacitor 80. The reference voltage generator 90 is a circuit for setting one of various levels of reference voltages, and the user interface unit 60 is configured as an operating switch or the like and used to input IPL output power from the user. The controller 50 adjusts a reference voltage of the reference voltage generator 90 according to a control signal outputted from the user interface unit 60, and generates a trigger signal at proper timing. The trigger unit 70 controls the radiation of a Xenon lamp into on and off operation by outputting a trigger operation signal for triggering the Xenon lamp flash unit 40 according to the trigger signal inputted from the controller 50, and the Xenon lamp flash unit 40 irradiates Xenon light on the user's skin according to the trigger operation signal. Further, the output of the noise filter 20 is used to supply stable power to the controller 50 via the constant voltage supplier 35. Generally, since the controller 50 uses a low operating voltage of 5V, it is possible to use the low-priced constant voltage supplier 35 having tens of watts, and thus it is even possible to use the inexpensive low-capacity noise filter 20 that removes noise from power supplied to the constant voltage supplier 35.

From now on, a circuit operation shown in FIG. 4 will be described. When FIG. 4 is described, a circuit that comprises a rectification unit 91, a smoothing unit 93, a constant current supply unit 38, and a constant voltage supply unit 35, which are selectively equipped, will be described as follows.

If the user inputs an output level through the user interface unit 60, a voltage level of the reference voltage generator 90 is set via the controller 50.

The inputted supply voltage 10 is supplied to the rectification unit 91, the constant current supply unit 38, and the constant voltage supply unit 35 after noise has been removed in the noise filter unit 20. The power inputted to the rectification unit is rectified into a DC component, is superposed with an AC component in the smoothing unit 93, and is provided to the double-voltage unit 110. The power from which noise is removed is inputted to the constant current supply unit 38, and a constant current is outputted to the reference voltage generator 90. After said noise-removed power has been inputted to the constant voltage supply unit 35, stable power is supplied to the controller 50.

The double-voltage unit 110 which has received the smoothed power outputs a peak value of the supply voltage double times or more, and the switch unit 120 compares the voltage inputted from the double-voltage unit 110, the voltage inputted to the reference voltage generator 90, and a voltage of an output end (input end of the charging capacitor). If a certain condition is satisfied, the switch unit is converted into the "on" state to charge the charging capacitor 80. The controller 50 generates a trigger signal by calculating proper timing. The trigger unit 70 outputs a trigger operation signal for triggering the Xenon lamp flash unit 40 according to the trigger signal inputted from the controller 50, and the Xenon lamp flash unit 40 irradiates Xenon light on the user's skin according to the trigger operation signal.

Figure 7:
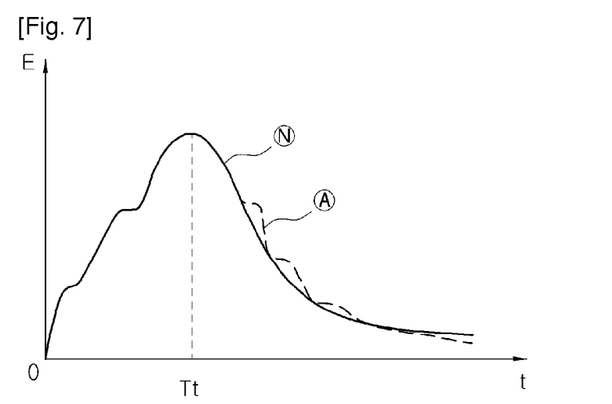
FIG. 7 is a graph for illustrating the amount of energy charged and discharged in a charging capacitor in accordance with time.

Meanwhile, in the circuit diagram of FIG. 4, it is illustrated that an input-blocking switch SW is added to the noise filter unit 20, and that a control signal for turning on and off a switch of the noise filter unit 20 is received from the controller 50. Said configuration will be described as follows. If the noise filter unit 20 which is not added with the switch is used, the energy is irregularly charged even when the charged energy is discharged to the Xenon lamp flash unit 40, thereby causing a problem that the energy supplied to the user's skin is not regular. Such a problem will be described in reference to FIG. 7. FIG. 7 is a graph for illustrating the amount of energy charged and discharged in a charging capacitor, wherein a horizontal axis indicates a time and a vertical axis indicates the amount of energy. A charging process is progressed until the time Tt from 0 second, and a discharging process is initiated by the trigger operation signal. Although a desirable discharging process is performed along a smooth curve marked as "(n)", if there is no switch in the noise filter unit 20 in the circuit diagram of FIG. 4, the charging process is progressed by the inputted supply voltage, so that the amount of energy like the curve "(a)" in FIG. 7 is supplied to the user.

To solve the charging problem during such a discharging period, the present invention shows two methods. One of the methods is to block the supply voltage inputted during the discharging process by using the controller 50 and the noise filter unit 20 having the switch SW illustrated in FIG. 4, and the other is to start discharging at a corresponding time matched with a certain period of the inputted supply voltage illustrated in FIG. 5.

In the circuit of FIG. 4, the controller 50 generates the control signal for turning off the input-blocking switch SW during the discharging time, and the noise filter unit 20 is blocked according to the control signal during the discharging time in order to prevent the inputted supply voltage from being supplied. Also, Xenon lamp are often continuous discharged when lamp driving circuit is out of order and PWM control cannot be controlled. At this time, it is possible not to supply continuous energy to Xenon lamp by changing "off" state on the switch SW. A relay operated by an electromagnet or a solid state relay (SSR) operated by a semiconductor has been used as the input-blocking switch SW. Compared with a circuit diagram of FIG. 5 to be mentioned later, the circuit diagram illustrated in FIG. 4 has an advantage that a special delay for matching timing is not generated. Since the input-blocking switch SW is a switch for preventing the charging capacitor 80 from being charged by the inputted supply voltage 10 while the charging capacitor 80 is discharged, it is also possible that said switch is provided at any position that can block the electric flow between the supply voltage 10 and the charging capacitor 80 in addition to the noise filter unit 20. That is to say, the input-blocking switch SW may be equipped at any place capable of switching the electric flow between the supply voltage and the charging capacitor. For instance, the input-blocking switch SW can be positioned even between the double-voltage unit 110 and the switch unit 120. Also, as another embodiment, it makes the same result of shutting off the power supplied to noise filter unit 20 if the reference voltage supplied to the switch unit 120 is controlled to be almost zero voltage.

Figure 5:
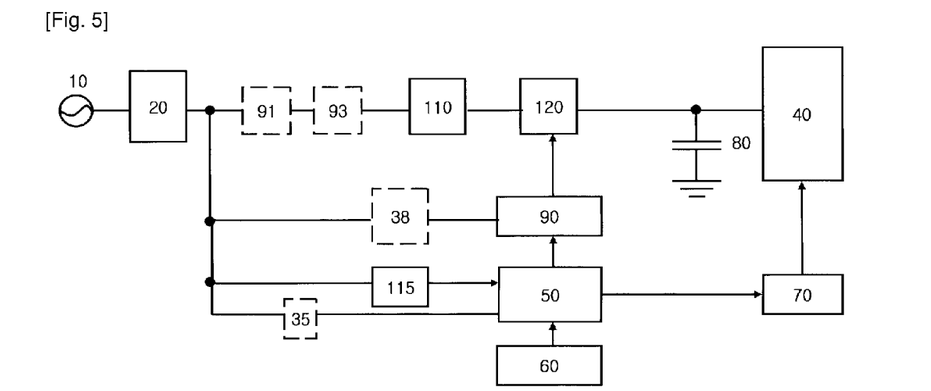
FIG. 5 is one embodiment of a driving circuit diagram of an IPL apparatus in accordance with the present invention.

FIG. 5 is one embodiment of a driving circuit diagram of an IPL apparatus in accordance with the present invention. Since the circuit diagram shown in FIG. 5 has almost similar configuration to the circuit diagram shown in FIG. 4, only the features different from those of the circuit diagram of FIG. 4 will be described below. The circuit diagram of FIG. 5 shows a noise filter unit 20 from which a switch is removed, and thus a control signal line inputted to the noise filter unit 20 from the controller 50 in FIG. 4 is unnecessary. Instead, in the circuit diagram of FIG. 5, an input wave timing unit 115, which receives an output signal of the noise filter unit 20 and generates an input wave timing signal at every time such as up or down time of an input waveform, is added between a controller 50 and the noise filter unit 20. Like shown in FIG. 8, the input wave timing unit 115 perceives the input waveform inputted from the noise filter unit 20, and outputs an input wave timing signal S to the controller 50 at every certain time, and the input wave timing unit can simply be realized by using a photo coupler. An output of the noise filter unit 20 is connected to a photo diode used as an input end of the photo coupler, the photo diode is turned on to generate light if more than a certain voltage is applied, and a light receiving transistor which constitutes an output end of the photo coupler is turned on by receiving the light generated from the photo diode and generates the input wave timing signal S.

Figure 8:
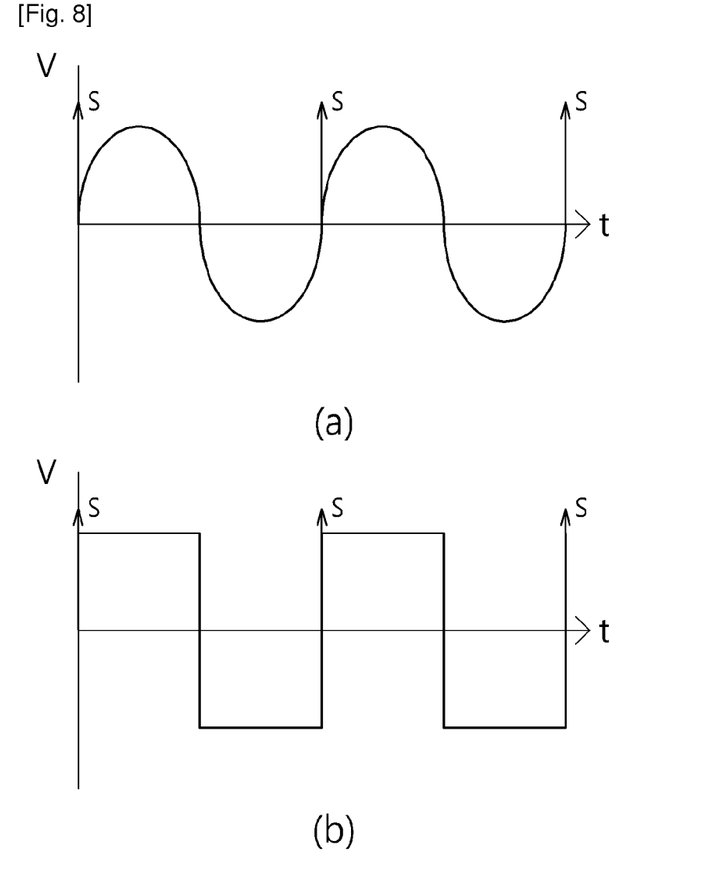
FIG. 8 is a waveform diagram for illustrating that an input wave timing unit outputs an input wave timing signal by using an input wave inputted from a noise filter unit.

FIG. 8(*a*) illustrates that the input wave timing signal S is outputted at every time whenever a sine wave is increased if the sine wave is inputted from the noise filter unit 20 to the input wave timing unit 115, and FIG. 8(*b*) illustrates an example that the input wave timing unit 115 generates a square wave from the input wave inputted from the noise filter unit 20, and that the input wave timing signal S is generated at every time whenever the square wave is increased and is applied to the controller 50.

If the input wave timing signal S is inputted from the input wave timing unit 115, the controller 50 which constitutes the circuit of FIG. 5 generates a trigger signal for starting discharging at a proper time and transmits the generated trigger signal to the trigger unit 70.

The driving circuit of the IPL apparatus in accordance with the one embodiment of the present invention shown in FIG. 4 and FIG. 5 has an advantage of using one of PAM and PWM driving modes if controller 50 controls the width of trigger signal or changes reference voltage setup without changing a circuit configuration, that is, through the same circuit configuration.

Figure 6:
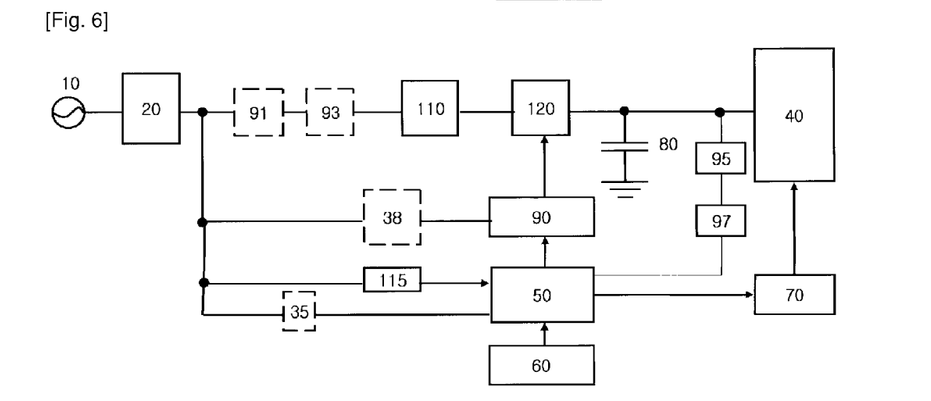
FIG. 6 is one embodiment of a driving circuit diagram of an IPL apparatus in accordance with the present invention.

FIG. 6 is one embodiment of a driving circuit diagram of an IPL apparatus in accordance with the present invention. Since the circuit diagram shown in FIG. 6 has almost similar configuration to the circuit diagram shown in FIG. 5, only the features different from those of the circuit diagram of FIG. 5 will be described below. The controller 50 in the circuit diagram shown in FIG. 4 and FIG. 5 calculates proper charging time and/or discharging time, and in the circuit diagram of FIG. 4, the trigger signal is generated by blocking the input signal of the noise filter unit 20, or in the circuit diagram of FIG. 5, the trigger signal is generated at a corresponding time matched with the input wave timing signal S outputted from the input wave timing unit 115. The circuit diagram of FIG. 6 is characterized in that a voltage divider 195 and an analog to digital converter 97 are additionally provided between a charging capacitor 80 and a controller 50 in order to exactly sense a voltage of the charging capacitor 80. The voltage divider 195 is a circuit element for measuring a charging voltage of the capacitor 80 while minimizing power consumption, and in the present invention, a voltage Vc of the capacitor 80 is divided within the range of approximately $1/10$ to $1/300$, and the divided voltage is inputted to the controller 50 through the analog to digital converter 97. The controller 50 in the circuit diagram of FIG. 6 senses a voltage level inputted from the analog to digital converter 97, and generates a trigger signal at a corresponding time matched with an input wave timing signal S outputted from an input wave timing unit 115. It is needless to say that the voltage divider 195 and the analog to digital converter 97 may be equipped in the circuit diagram of FIG. 4, and in this case, the controller 50 generates the trigger signal by blocking the input signal of the noise filter unit 20 if the charging capacitor 80 reaches a desired voltage level.

Figure 9:
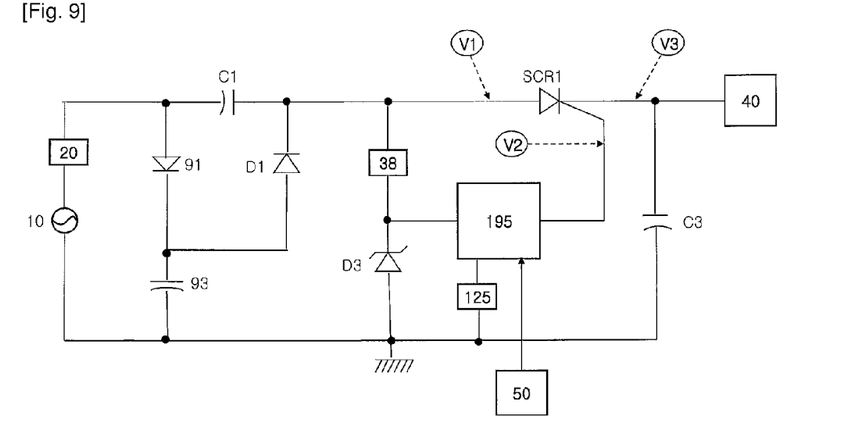
FIG. 9 is one embodiment of a driving circuit diagram of an IPL apparatus in accordance with the present invention.

FIG. 9 is one embodiment of a driving circuit diagram of an IPL apparatus in accordance with the present invention. In the circuit diagram of FIG. 9, for the explanatory convenience, only the main circuit configurations such as a noise filter unit 20, a rectification unit 91, a smoothing unit 93, a double-voltage unit, a constant current supply unit 38, a reference voltage generator, a switch unit, a charging capacitor, a controller 50, and a Xenon lamp flash unit 40 are illustrated, and the rest of circuit elements were omitted. In the circuit diagram of FIG. 9, a supply voltage 10 corresponds to the supply voltage 10 of FIG. 4, a noise filter unit 20, a rectification unit 91, and a smoothing unit 93 respectively correspond to the noise filter unit 20, the rectification unit 91, and the smoothing unit 93 of FIG. 4, a capacitor C1 and a diode D1 correspond to the double-voltage unit 110 of FIG. 4, a Zener diode D3, a Zener temperature compensation circuit unit 125, and a voltage divider 195 correspond to the reference voltage generator 90 of FIG. 4, an SCR 1 corresponds to the switch unit 120 of FIG. 4, and a capacitor C3 corresponds to the charging capacitor 80 of FIG. 4.

Figure 10:
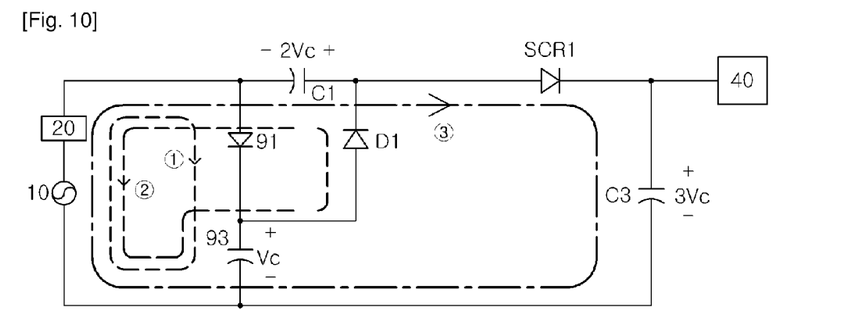
FIG. 10 is a partial circuit of FIG. 9, and shows a circuit diagram for illustrating double voltages.

First, a double-voltage circuit for boosting a voltage triple times will be described as follows. FIG. 10 separately illustrates only the double-voltage circuit which only comprises the supply voltage 10, the noise filter 20, rectification unit 91, smoothing unit 93, the capacitors C1 and C3, the diode D1, and the SCR 1 in the circuit of FIG. 9.

First, when the supply voltage 10 supplies "+" voltage, current path "①" flowing through the noise filter 20, rectification unit 91, and smoothing unit 93 is formed. And capacitor consisting of rectification unit 91 is charged Vc voltage with the polarity as shown FIG. 10.

Then, when the supply voltage changes "−" voltage, current path "②" flowing through the noise filter 20, capacitor C1, diode D1 and smoothing unit 93 is formed. Charges (or energies) accumulated at Smoothing unit 93 is accumulated to capacitor C1 through the diode D1 and the charges supplied from the supply voltage 10 are also accumulated to the capacitor C1 simultaneously. Therefore the capacitor C1 is charged to 2Vc voltage (almost double voltage of the supply voltage 10) with the polarity as shown FIG. 10.

When the supply voltage is changed "−" to "+" in the "on" state of thyristor SCR1, new current path "③" flowing through noise filter 20, capacitor C1, thyristor SCR1 and charging capacitor C3 is formed beside current path "①". At this time, the accumulated charges (or energies) at capacitor C1 are moved to charging capacitor C3 through the thyrister SCR1 and energy supplied by the supply voltage 10 also accumulated to charging capacitor C3. Therefore, 3Vc voltages (almost triple voltage of the supply voltage 10) are accumulated to charging capacitor C3 as shown in FIG. 10. As shown in FIG. 10, we can see that rectification unit 91 and smoothing unit 93 according to the present invention also contribute to form double voltage.

Figure 11:
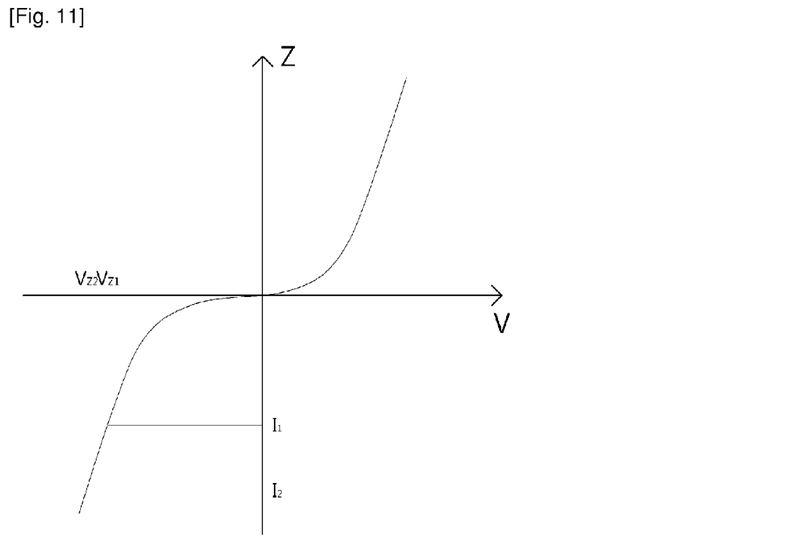
FIG. 11 is a graph for illustrating a characteristic of voltage to current operation of a Zener diode.

Again, in FIG. 9, the Zener diode D3 and the voltage divider 195 form a reference voltage generator. The Zener diode is a circuit element for maintaining a certain voltage all the time, and the certain voltage applied to the Zener diode D3 generates a reference voltage in accordance with an energy level inputted to a gate terminal of the SCR 1 through a user interface by the voltage divider 195 which is formed with a plurality of switch elements and a plurality of resistors. However, said Zener diode may cause a voltage change if an applied current value is not regular. Such a problem will be described in reference to FIG. 11. FIG. 11 is a graph for illustrating a characteristic of voltage to current operation of a Zener diode. Like shown in FIG. 11, it could be understood that if a current which flows in the Zener diode is changed into I2 from I1, a voltage value applied thereto is also changed into V2 from V1. To solve such a problem, the constant current supply unit 38 is employed in FIG. 9, and said constant current supply unit 38 may simply be configured as a resistance and constant current diode.

Another problem of the Zener diode D3 is a draft that a voltage gets higher when the peripheral temperature rises. Said voltage draft problem in accordance with the temperature rise may be solved by using a Zener temperature compensation circuit unit 125 in the circuit diagram of FIG. 9, which is positioned between the voltage divider 195 and a ground and is characterized by lowering a resistance value according to the rise of the peripheral temperature. A thermistor may be used as the Zener temperature compensation circuit unit 125, and the thermistor performs a function of compensating the voltage increase which occurs in the Zener diode D3 owing to the temperature rise, whereby the Zener diode D3 operates as a stable reference voltage source irrespective of the peripheral temperature change.

Even though the circuit diagram of FIG. 9 shows that the reference voltage generator is configured with the Zener diode D3, the Zener temperature compensation circuit unit 125, and the voltage divider 195, it is also possible to form only the voltage divider if the precision of a reference voltage may be sacrificed slightly. In addition, as another configuration, it is also possible to comprise a digital to analog converter between the controller and the gate terminal of the SCR, and to convert a voltage level value inputted from the controller by using the digital to analog converter and to apply the converted value to the gate terminal of the SCR.

Next, the operation of the SCR (SCR 1, thyristor) will be described as follows. Although the thyristor (SCR 1) is used as a switch in the circuit diagram of FIG. 9, said thyristor could be replaced with a triac element. An anode of the thyristor (SCR 1) is connected to one terminal of the capacitor C1 which forms the double-voltage unit, and a voltage of the anode is marked "V1". A cathode of the thyristor (SCR 1) is connected to one terminal of the charging capacitor C3, and a voltage of the cathode is marked "V3", and a voltage of the gate terminal which is the remaining terminal of the thyristor (SCR 1) is marked "V2". A reference voltage which can be set to the gate voltage "V2" of the thyristor (SCR 1) is determined by a value between maximum and minimum values of the voltage "V1" applied to the anode terminal. The thyristor SCR 1 shown in FIG. 9 is turned on when "V1" has a larger value than "V3" and "V2" has a larger voltage than "V3" as much as the threshold voltage.

After the thyristor SCR 1 is turned on, "V1" gets lower than "V3" then, thyristor SCR 1 is turned off. And even if "V1" gets higher than "V3" while "V2" has a lower value than "V3", the thyristor SCR 1 cannot be turned on. Therefore charging process is stopped. At this time, the value "V3" is same value of gate threshold minus from the value "V2". Therefore the value "V3" becomes similar value "V2".

Normally, a rectification unit 91 and a smoothing unit 93 in the circuit configuration shown in FIG. 9 and FIG. 10 are contributed to form double voltage and the voltage charged to charging capacitor C3 becomes almost triple the voltage of the supply voltage 10. Therefore the circuit configuration shown in FIG. 9 and FIG. 10 is usually used at the area with 100V~120V of the supply voltage 10.

Figure 12:
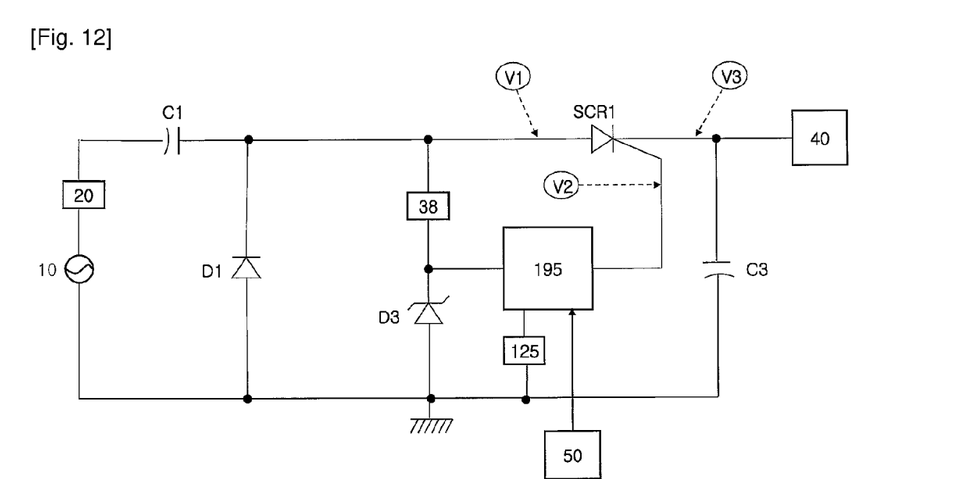
FIG. 12 is one embodiment of a driving circuit diagram of an IPL apparatus in accordance with the present invention.
Figure 13:
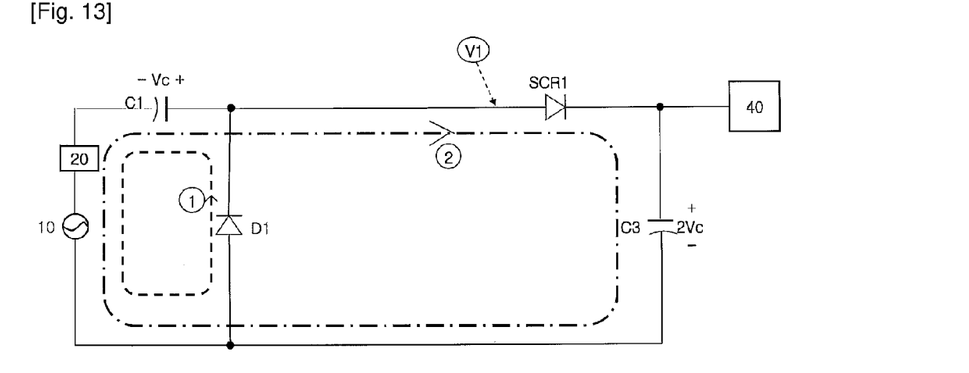
FIG. 13 is a partial circuit of FIG. 12, and shows a circuit diagram for illustrating double voltages.

On the other hand, almost double energy supplied by supply voltage 10 can be charged to charging capacitor C3 in the area with 220V of the supply voltage 10. The circuit configuration excepting a rectification unit 91 and a smoothing unit 93 is proposed in FIG. 12 and FIG. 13. This circuit configuration is suitable to the area with 220V of the supply voltage 10. FIG. 12 is correspond to FIG. 9 and FIG. 13 is correspond to FIG. 10.

When the supply voltage 10 supplies "−" voltage, current path as shown number "①" flowing through the noise filter 20, capacitor C1, and diode D1 is formed. Therefore capacitor C1 is charged Vc voltage (almost the voltage supplied from supply voltage 10) with the polarity as shown FIG. 13.

If the supply voltage is changed "+" to "−" in the "on" state of thyristor SCR1, current path "②" flowing through noise filter 20, capacitor C1, thyristor SCR1 and charging capacitor C3 is formed. At this time, the accumulated charges (or energies) at capacitor C1 are moved to charging capacitor C3 through the thyrister SCR1 and energy supplied by the supply voltage 10 is also accumulated to charging capacitor C3. Therefore, 2Vc voltages (almost double voltage of the supply voltage 10) are accumulated to charging capacitor C3 as shown in FIG. 13.

Hereinafter, the operation of the circuit shown in FIG. 13 will be described below.

First, suppose that 60 Hz of 220V power is used as a supply voltage, a reference voltage of 340V is applied to a gate of the thyristor (SCR 1) by the combination of the voltage divider in accordance with an energy level which is set by the user through the user interface, no electric charges are accumulated in the charging capacitor in an early state, and that the threshold voltage of the thyristor (SCR 1) is 0V. Under said condition, a maximum peak value of the corresponding supply voltage is 310V approximately. Since electric charges supplied by the supply voltage 10 is doubled with the electric charges accumulated in the capacitor C1, a bias voltage of the "V1" terminal is 310V and the amplitude is 310V. Further, a voltage varying between 0V and 620V is applied to the "V1" terminal because a sine-wave voltage having a maximum peak value of 620V is applied.

If the supply voltage is applied under said condition, the anode voltage of the thyristor (SCR 1) gets higher than the cathode voltage (V1>V3) and the gate voltage V2 gets higher than the threshold voltage for turning on the thyristor compared with the cathode voltage V3. Thus, the thyristor is conducted to charge the charging capacitor. If the waveform applied to the V1 terminal gets lower than the cathode voltage (charging voltage of the charging capacitor) while going down by passing through the peak, the thyristor (SCR 1) stops operating. Then, as the input waveform starts increasing in the next cycle, the anode voltage V1 of the thyristor (SCR 1) gets higher than the voltage V3 of the cathode terminal of the thyristor (SCR 1), and under the condition "V2>V3", the thyristor (SCR 1) is conducted again to progress the charging process.

The charging process is progressed as said operation is repeated until the voltage charged in the charging capacitor C3 reaches a voltage which is subtracted as much as the threshold voltage for turning on the thyristor (SCR 1) from the reference voltage applied to the gate of the thyristor (SCR 1). Then, power is supplied to the Xenon lamp flash unit 40 by a trigger operation signal which is not shown in FIG. 12.

While specific embodiments of the invention have been described and shown above, it is obvious that the invention can be modified in various forms by those skilled in the art without departing from the technical spirit of the invention. The modified embodiments should not be understood separately from the spirit and scope of the invention and should be considered as belonging to the appended claims of the invention. Although the audio communication has been mainly described above, the invention can be easily applied to a video communication. In this case, the phone 500 means a television phone and a protocol suitable for a video should be used instead of the SIP protocol.

The invention claimed is:

1. An intense pulsed light apparatus, comprising:
    a voltage doubler which comprises a first capacitor, and outputs a higher voltage than an inputted supply voltage to the voltage doubler by superposing the inputted supply voltage with a voltage charged in the first capacitor;
    a storage capacitor which charges energy for turning on a Xenon lamp by accumulating electric charges supplied from the voltage doubler;
    a reference voltage generator which sets a charging voltage level charged in the storage capacitor and outputs the charging voltage level; and
    a switch positioned between the voltage doubler and the storage capacitor, and switches on and off movement of electric charges to the storage capacitor from the voltage doubler,
    wherein the switch switches on and off the movement of electric charges based on the voltage outputted from the voltage doubler, the charging voltage level outputted from the reference voltage generator, and a voltage of the storage capacitor,
    the first capacitor is directly connected to a first terminal of the switch, and
    a first output terminal of the switch is directly connected to the Xenon lamp and the storage capacitor.

2. The intense pulsed light apparatus of claim 1, further comprising:
    a rectifier which includes a first terminal connected to a first terminal of the inputted supply voltage and rectifies an alternating current (AC) of the inputted supply voltage into a direct current (DC); and
    a smoothing circuit which is connected between a second terminal of the rectifier and a second terminal of the inputted supply voltage, the smoothing circuit being charged into a peak voltage level of the inputted supply voltage at a time when current flows to the smoothing circuit through the rectifier, and the smoothing circuit supplies the peak voltage level charged in the smoothing circuit to the voltage doubler at a time when current flows from the second terminal of the inputted supply voltage to the second terminal of the rectifier;
    wherein the voltage doubler has two input terminals and one output terminal, the two input terminals of the voltage doubler are connected to the rectifier in shunt and the one output terminal of the voltage doubler is connected to the switch.

3. The intense pulsed light apparatus of claim 2, further comprising a constant current supply which supplies a predetermined current to the reference voltage generator and is connected to the reference voltage generator;
    wherein the reference voltage generator comprises a Zener diode and a voltage divider.

4. The intense pulsed light apparatus of claim 3, further comprising:
    a user interface which receives an adjustment signal for the amount of desired energy of Xenon lamp light from a user;
    a controller which outputs a trigger signal having a width or an interval which is adjusted according to the adjustment signal inputted through the user interface;
    a trigger circuit which outputs a trigger operation signal according to the trigger signal outputted from the controller; and
    a Xenon lamp flash circuit which turns on and off the Xenon lamp by using energy charged in the storage capacitor according to the trigger operation signal.

5. The intense pulsed light apparatus of claim 4, further comprising a voltage divider and an analog to digital converter which are disposed between the controller and a terminal located between a Xenon lamp flash circuit and an output terminal of the storage capacitor.

6. The intense pulsed light apparatus of claim 4, further comprising an input-blocking switch which switches electric connection between the inputted supply voltage voltage and the storage capacitor and is disposed between the inputted supply voltage and the storage capacitor, and the controller turns off the input-blocking switch while the storage capacitor is discharged.

7. The intense pulsed light apparatus of claim 6, further comprising an input wave timing circuit which perceives a waveform of the inputted supply voltage between the inputted supply voltage and the controller and generates an input wave timing signal generated at a time when the inputted supply voltage shows a predetermined waveform, and the controller outputs a trigger signal so that the trigger signal is matched with the input wave timing signal.

8. The intense pulsed light apparatus of claim 7, wherein the controller varies a voltage of the reference voltage generator according to an input value of the user which is inputted through the user interface.

9. The intense pulsed light apparatus of claim 1, wherein the switch includes a thyristor or a triac.

\* \* \* \* \*